(12) United States Patent
Li (10) Patent No.: US 12,290,397 B1
(45) Date of Patent: *May 6, 2025

(54) ULTRASOUND-BASED LIVER EXAMINATION DEVICE, ULTRASOUND APPARATUS, AND ULTRASOUND IMAGING METHOD

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventor: Shuangshuang Li, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,372

(22) Filed: Dec. 22, 2023

Related U.S. Application Data

(63) Continuation of application No. 17/174,089, filed on Feb. 11, 2021, now Pat. No. 11,890,133, which is a
(Continued)

(51) Int. Cl.
*A61B 8/08* (2006.01)
*A61B 8/00* (2006.01)

(52) U.S. Cl.
CPC .............. *A61B 8/08* (2013.01); *A61B 8/463* (2013.01); *A61B 8/5207* (2013.01); *A61B 8/5223* (2013.01); *A61B 8/5269* (2013.01)

(58) Field of Classification Search
CPC .......... A61B 8/08; A61B 8/463; A61B 8/5207; A61B 8/5223; A61B 8/5269
See application file for complete search history.

(56) References Cited

U.S. PATENT DOCUMENTS

| 5,511,423 A | | 4/1996 | Sugiyama et al. |
| 6,063,030 A | * | 5/2000 | Vara ................ A61B 8/465 |
| | | | 600/440 |

(Continued)

FOREIGN PATENT DOCUMENTS

| CN | 101160099 A | 4/2008 |
| CN | 101606853 A | 12/2009 |

(Continued)

OTHER PUBLICATIONS

PCT International Search Report and the Written Opinion mailed May 29, 2019, issued in related International Application No. PCT/CN2018/103078, with partial English translation (10 pages).
(Continued)

*Primary Examiner* — Sanjay Cattungal
(74) *Attorney, Agent, or Firm* — Sheppard Mullin Richter & Hampton LLP (57) ABSTRACT

An ultrasound apparatus, ultrasound-based liver examination device and ultrasound imaging method are provided. The ultrasound apparatus may include: an ultrasound probe, a transmission and receiving controller, an ultrasound echo signal processor, a data processor and a display device. The ultrasound echo signal processor may perform different processes on an ultrasound echo signal according to usage of the ultrasound echo signal. A gain compensation for enhancing image quality may be performed on a first ultrasound echo signal to be used for obtaining the ultrasound image, and a gain compensation for preserving original information may be performed on a second ultrasound echo signal to be used for calculating a quantitative parameter of a liver. The
(Continued)

data processor may generate the ultrasound image according to the processed first ultrasound echo signal, calculate the quantitative parameter according to the processed second ultrasound echo signal, and output the ultrasound image and the quantitative parameter.

20 Claims, 3 Drawing Sheets

Related U.S. Application Data continuation of application No. PCT/CN2018/103078, filed on Aug. 29, 2018.

(56) References Cited

U.S. PATENT DOCUMENTS

| | | | |
|---|---|---|---|
| 6,261,234 B1* | 7/2001 | Lin | A61B 8/445 600/463 |
| 6,468,212 B1* | 10/2002 | Scott | A61B 8/463 600/440 |
| 9,060,737 B2 | 6/2015 | Matsumura et al. | |
| 9,072,471 B2* | 7/2015 | Kato | A61B 8/462 |
| 9,314,225 B2* | 4/2016 | Steen | A61B 8/5207 |
| 9,568,598 B2 | 2/2017 | Okamura et al. | |
| 2003/0195418 A1* | 10/2003 | Barnes | A61B 8/462 600/437 |
| 2005/0085730 A1* | 4/2005 | Flesch | A61B 8/12 600/459 |
| 2006/0020204 A1* | 1/2006 | Serra | G01S 7/5208 600/437 |
| 2010/0160787 A1* | 6/2010 | Gorzitze | A61M 5/427 600/461 |
| 2010/0217128 A1* | 8/2010 | Betts | A61B 8/4254 345/184 |
| 2012/0133601 A1* | 5/2012 | Marshall | G06F 3/041 345/173 |
| 2012/0209115 A1 | 8/2012 | Tonomura | |
| 2012/0259225 A1 | 10/2012 | Tashiro | |
| 2013/0226001 A1* | 8/2013 | Steen | G01S 7/52096 600/447 |
| 2013/0239052 A1* | 9/2013 | Moody | G06F 3/017 715/810 |
| 2013/0324850 A1* | 12/2013 | Petruzzelli | A61B 8/465 600/407 |
| 2014/0051984 A1* | 2/2014 | Berger | A61B 18/02 600/424 |
| 2014/0121524 A1* | 5/2014 | Chiang | A61B 8/463 600/459 |
| 2014/0243669 A1* | 8/2014 | Halmann | G01S 7/5208 600/443 |
| 2015/0265252 A1* | 9/2015 | Chu | A61B 8/461 600/431 |
| 2017/0150948 A1* | 6/2017 | Kanayama | A61B 8/488 |

FOREIGN PATENT DOCUMENTS

| | | |
|---|---|---|
| CN | 101987023 A | 3/2011 |
| CN | 102596052 A | 7/2012 |
| CN | 103479398 A | 1/2014 |
| CN | 104873221 A | 9/2015 |
| JP | H07-23959 A | 1/1995 |
| JP | 2007-236740 A | 9/2007 |
| WO | 2007-148735 A1 | 12/2007 |

OTHER PUBLICATIONS

PCT International Preliminary Report on Patentability mailed Mar. 11, 2021, issued in related International Application No. PCT/CN2018/103078, with English translation (12 pages).
First Search dated Apr. 24, 2022, issued in related Chinese Application No. 201880095877.X (3 pages).
Supplementary Search dated Oct. 25, 2022, issued in related Chinese Application No. 201880095877.X (2 pages).
Non-Final Office Action dated Jun. 8, 2023, issued in related U.S. Appl. No. 17/174,089 (9 pages).

* cited by examiner

ULTRASOUND-BASED LIVER EXAMINATION DEVICE, ULTRASOUND APPARATUS, AND ULTRASOUND IMAGING METHOD

CROSS REFERENCE TO RELATED APPLICATIONS

This application is a continuation application of U.S. patent application Ser. No. 17/174,089, filed on Feb. 11, 2021, and entitled "ULTRASOUND-BASED LIVER EXAMINATION DEVICE, ULTRASOUND APPARATUS, AND ULTRASOUND IMAGING METHOD", which is a continuation of International Patent Application No. PCT/CN2018/103078, filed with the China National Intellectual Property Administration (CNIPA) of People's Republic of China on Aug. 29, 2018, and entitled "ULTRASOUND-BASED LIVER EXAMINATION DEVICE, ULTRASOUND APPARATUS, AND ULTRASOUND IMAGING METHOD". The entire content of the above-identified applications are incorporated herein by reference.

TECHNICAL FIELD

The present disclosure relates to an ultrasound apparatus, and in particular to an ultrasound-based liver examination device and an ultrasound method for detecting hepatic steatosis.

BACKGROUND

Hepatic steatosis is also referred to as fatty liver disease, and is a pathological change of excessive fat accumulation in liver cells caused by various reasons. Fatty liver disease is seriously endangering human health, becomes the second largest liver disease after viral hepatitis, and has been recognized as a common cause of hidden hepatic cirrhosis. In general, hepatic steatosis is a reversible disease, and the clinical manifestations are asymptomatic in mild cases and fierce in severe cases. Therefore, the early diagnosis and timely treatment of hepatic steatosis are of great significance.

At present, ultrasound diagnosis is the first choice for the diagnosis of hepatic steatosis, and is widely used in physical examination and screening. Its diagnostic indicators mainly include: the degree of echo difference of liver and kidney tissues, the degree of near and far field echo difference of the liver, the clarity of blood vessels in the liver, the degree of enlargement of the liver, etc. However, these indicators are generally qualitative diagnostic indicators, and are directly related to factors such as the operating experience of operating doctors and the subjective perception of brightness. Although there are some techniques that can give quantitative parameters to evaluate hepatic steatosis, only a certain quantitative parameter can be given alone.

SUMMARY

The present application provides an ultrasound apparatus and an ultrasound-based hepatic steatosis detection device and ultrasound imaging method for improving the accuracy of diagnosing hepatic steatosis.

In an embodiment, an ultrasound apparatus is provided, comprising:
an ultrasound probe configured to transmit an ultrasound wave to a target tissue and receive an ultrasound echo from the target tissue, wherein the target tissue is a tissue of a liver;
a transmission and receiving controller configured to control the ultrasound probe to transmit the ultrasound wave to the target tissue and receive the ultrasound echo to obtain an ultrasound echo signal;
an ultrasound echo signal processor configured to perform different processes on the obtained ultrasound echo signal according to usage of the obtained ultrasound echo signal, wherein, a gain compensation for enhancing image quality is performed on a first ultrasound echo signal to be used for obtaining an ultrasound image of the target tissue, and a gain compensation for preserving original information is performed on a second ultrasound echo signal to be used for calculating a quantitative parameter of the liver;
a data processor configured to generate the ultrasound image of the target tissue according to the processed first ultrasound echo signal, calculate the quantitative parameter of the liver according to the processed second ultrasound echo signal, and output the ultrasound image and the quantitative parameter; and
a display device configured to display the ultrasound image and the quantitative parameter.

In an embodiment, an ultrasound-based liver examination device is provided, comprising:
a receiving circuit configured to acquire an ultrasound echo signal which is obtained by scanning a target tissue with an ultrasound wave, wherein the target tissue is a tissue of a liver;
an ultrasound echo signal processor configured to perform different processes on the obtained ultrasound echo signal according to usage of the obtained ultrasound echo signal, wherein a gain compensation for enhancing image quality is performed on a first ultrasound echo signal to be used for obtaining an ultrasound image of the target tissue and a gain compensation for preserving original information is performed on a second ultrasound echo signal to be used for calculating a quantitative parameter of the liver; and
a data processor configured to generate the ultrasound image of the target tissue according to the processed first ultrasound echo signal and calculate the quantitative parameter of the liver according to the processed second ultrasound echo signal.

In an embodiment, an ultrasound imaging method is provided, comprising:
transmitting an ultrasound wave to a target tissue and receiving an ultrasound echo from the target tissue to obtain an ultrasound echo signal, the target tissue being a tissue of a liver;
performing a gain compensation for enhancing image quality on a first ultrasound echo signal to be used for obtaining an ultrasound image of the target tissue;
performing a gain compensation for preserving original information on a second ultrasound echo signal to be used for calculating a quantitative parameter of the liver;
generating the ultrasound image of the target tissue according to the processed first ultrasound echo signal;
calculating the quantitative parameter of the liver according to the processed second ultrasound echo signal; and
displaying the ultrasound image and the quantitative parameter.

According to an ultrasound apparatus and an ultrasound-based liver detection device in the above embodiments, it is possible to calculate the corresponding quantitative evaluation parameters based on the original ultrasound echo signal while displaying the B-mode ultrasound image of the biological tissue. The B-mode ultrasound image and the quantitative parameter are combined, thereby reducing the impact of the experiences and subjective feelings of doctors, and improving the accuracy of diagnosing hepatic steatosis.

DESCRIPTION OF THE PREFERRED EMBODIMENTS

The present disclosure will be further described in detail below through specific implementations in conjunction with the accompanying drawings. Associated similar element reference numerals are used for similar elements in different implementations. In the following implementations, many details are described such that the present application can be better understood. However, it may be effortlessly realized by a person skilled in the art that some of the features may be omitted, or may be substituted by other elements, materials, and methods in different cases. In certain cases, some operations involved in the present disclosure are not displayed or described in the specification, which is to prevent a core part of the present disclosure from being obscured by too much description. Moreover, for a person skilled in the art, the detailed description of the involved operations is not necessary, and the involved operations can be thoroughly understood according to the description in the specification and the general technical knowledge in the art.

In addition, the characteristics, operations, or features described in the specification can be combined in any appropriate manner to form various implementations. Moreover, the steps or actions in the method description can also be exchanged or adjusted in order in a way that is obvious to a person skilled in the art. Therefore, the various orders in the specification and the accompanying drawings are merely for the purpose of clear description of a certain embodiment and are not meant to be a necessary order unless otherwise stated that a certain order must be followed.

The serial numbers themselves for the components herein, for example, "first" and "second", are merely used to distinguish the described objects, and do not have any sequential or technical meaning. Moreover, as used in the present disclosure, "connection" or "coupling", unless otherwise specified, comprises both direct and indirect connections (couplings).

Figure 1:
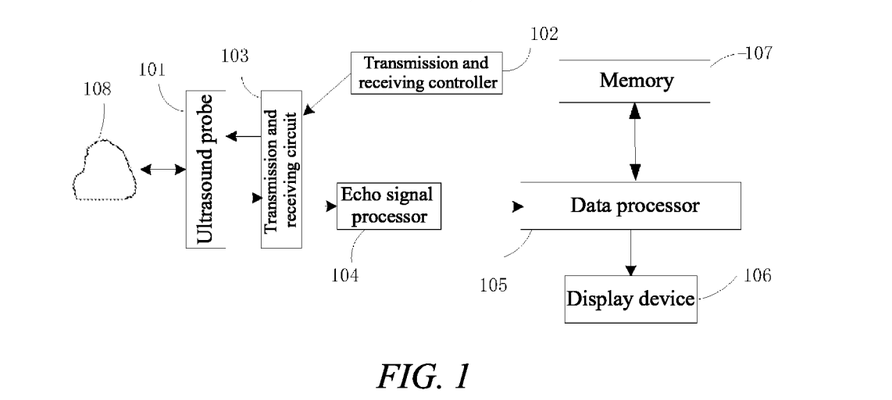
FIG. 1 is a structural schematic diagram of an ultrasound hepatic steatosis detection apparatus.

Referring to FIG. 1, the structure of an ultrasound apparatus 100 is as shown in FIG. 1, comprising an ultrasound probe 101, a transmission and receiving controller 102, a data processor 105, a display device 106 and a memory 107. In a specific embodiment, the ultrasound elasticity detection apparatus 100 further comprises a transmission and receiving circuit 103 and an ultrasound echo signal processor 104. The transmission and receiving controller 102 is in a signal connection with the ultrasound probe 101 by means of the transmission and receiving circuit 103, the ultrasound probe 101 is in a signal connection with the ultrasound echo signal processor 104 by means of the transmission and receiving circuit 103, an output end of the ultrasound echo signal processor 104 is connected to the data processor 105, and an output end of the data processor 105 is connected to the display device 106. The memory 107 is connected to the data processor 105.

The ultrasound probe 101 comprises a plurality of transducers which are also referred to as array elements, and the plurality of transducers are used to implement the mutual conversion of an electric pulse signal and ultrasound waves so as to transmit ultrasound waves to a biological tissue (e.g., a biological tissue in a human or animal body) 108 to be detected and receive ultrasound echoes reflected by the biological tissue. The plurality of transducers can be arranged in a row to form a linear array, or arranged in a two-dimensional matrix to form an area array, and the plurality of transducers can also form a convex array. The transducers can transmit ultrasound waves excited by electric signals, or transform the received ultrasound echoes into electric signals. Therefore, each of the transducers can be either used to transmit ultrasound waves to a region of interest of a biological tissue, or used to receive ultrasound echoes reflected from the region of interest of the biological tissue. When ultrasound detection is performed, a transmission sequence and a receiving sequence can control which transducers are used to transmit ultrasound and which transducers are used to receive ultrasound, or a transmission sequence and a receiving sequence can control the transducer to be used to transmit ultrasound waves or receive ultrasound echoes in a time slotted manner. All the transducers participating in ultrasound transmission can be simultaneously excited by the electric signal so as to simultaneously transmit ultrasound waves; or the transducers participating in ultrasound transmission can also be excited by several electric signals with a certain time interval, so as to continuously transmit ultrasound waves with a certain time interval.

The transmission and receiving controller 102 is used to generate a transmission/receiving sequence and output the transmission/receiving sequence to the ultrasound probe. The transmission sequence is used to control some or all of a plurality of array elements to transmit ultrasound waves to a region of interest of a biological tissue. The transmission sequence also provides transmission parameters (e.g., the amplitude, frequency, number of transmission, angle of transmission, mode and/or focused location, etc. of ultrasound waves). According to different purposes, the mode, transmission direction and focused location of the transmitted ultrasound can be controlled by means of adjusting the transmission parameters. The species of ultrasound waves may be pulse ultrasound waves, plane ultrasound waves, etc. The receiving sequence is used to control some or all of the plurality of array elements to receive ultrasound echoes reflected from the region of interest of the biological tissue.

The transmission and receiving circuit 103 is connected among the ultrasound probe and the transmission and receiving controller 102 and the ultrasound echo signal processor 104, and is used to transfer the transmission/receiving sequence controlled by the transmission and receiving controller 102 to the ultrasound probe 101 and transfer ultrasound echo signal received by the ultrasound probe 101 to the ultrasound echo signal processor 104.

The ultrasound echo signal processor 104 is used to process the ultrasound echo signal, for example, to perform filtering, amplification, beamforming and other processing for the ultrasound echo signal, so as to obtain ultrasound echo data. In a specific embodiment, the ultrasound echo signal processor 104 can be used to output the ultrasound echo data to the data processor 105, and can also firstly store the ultrasound echo data in the memory 107, such that when it is necessary to perform operation on the basis of the ultrasound echo data, the data processor 105 can read the ultrasound echo data from the memory 107.

The memory 107 is used to store data and programs. The programs include a system program of the ultrasound apparatus, various application programs, or algorithms for realizing various specific functions.

The data processor 105 is used to acquire the ultrasound echo data after the ultrasound echo being processed, and generate an ultrasound image according to the processed ultrasound echo data. For example, a B-mode image or a C-mode image.

The display device 106 is used to display detection results, for example, ultrasound images, calculation results, graphic charts or text description.

In the concept of the present disclosure, it is possible to generate an ultrasound image based on ultrasound echo data, and also quantitatively calculate the quantitative parameters for evaluation of hepatic steatosis based on the ultrasound echo data, which can not only obtain quantitative parameters of the liver, but also visually observe the position and the image of the liver, such that a doctor can combine the ultrasound image with these quantitative parameters to make judgments, so as to minimize the influence of the doctor's experience and subjective feelings, and ultimately improve the accuracy of the diagnosis of hepatic steatosis.

When the ultrasound waves enter the target tissue from shallow to deep, the ultrasound waves will be attenuated to different degrees, and the reflected ultrasound echo will also be attenuated to different degrees. In order to improve the quality of the image formed by the reflected ultrasound echo signals, gain compensation with different degrees is usually performed on the ultrasound echo signals in the ultrasound echo signals being processed stage. The depth of a positon where the ultrasound echo corresponding to the ultrasound echo signals is obtained in the target tissue is different, and the gain coefficient is also different, for example: the deeper the depth of the positon where the ultrasound echo corresponding to the ultrasound echo signals is obtained in the target tissue is, the greater the gain coefficient is, that is, the greater the magnification of the amplitude of the ultrasound echo signals is, such that the brightness of the ultrasound image displayed on the display interface tends to be consistent. Although this gain compensation method can improve the quality of the ultrasound image, it also loses some of the original information of the ultrasound echo signal, and some of the quantitative parameters used to evaluate hepatic steatosis will be affected, resulting in inaccurate calculation results. Therefore, in the embodiments of the present disclosure, the obtained ultrasound echo signal is subjected to different echo processes according to usage of the obtained ultrasound echo signal, for example, the gain compensation for the purpose of enhancing image quality is performed on the first ultrasound echo signal to be used for obtained an ultrasound image of the target tissue, and the gain compensation for the purpose of preserving original information (e.g., preserving ultrasound attenuation information, ultrasound echo signal-to-noise ratio information, etc.) is performed on the second ultrasound echo signal to be used for calculating the quantitative parameter of the liver. The present disclosure will be described in detail below with the specific embodiments.

Figure 2:
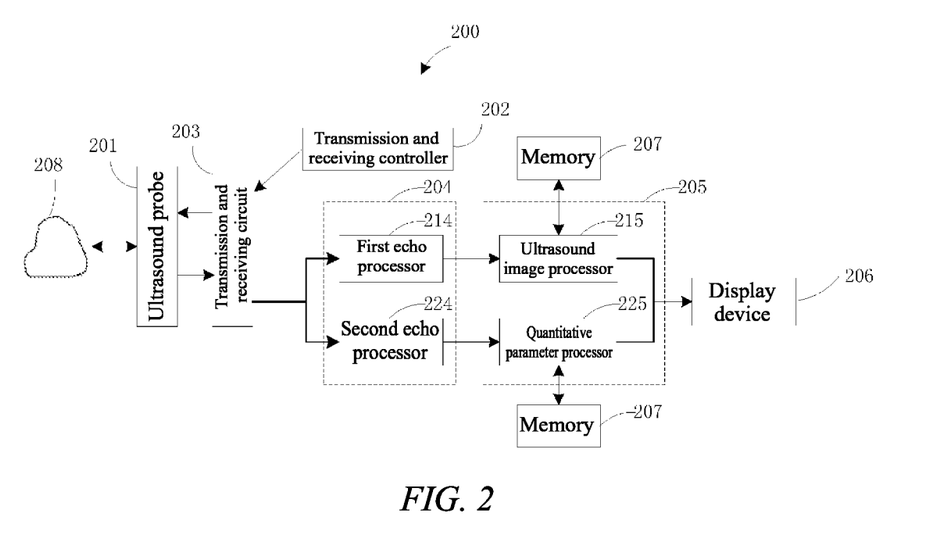
FIG. 2 is a structural schematic diagram of an ultrasound hepatic steatosis detection apparatus in an embodiment.

Referring to FIG. 2, in an embodiment, the ultrasound apparatus 200 comprises an ultrasound probe 201, a transmission and receiving controller 202, a transmission and receiving circuit 203, an ultrasound echo signal processor 204, a data processor 205, a display device 206 and a memory 207. The ultrasound echo signal processor 204 comprises a first echo processor 214 and a second echo processor 224. The data processor 205 comprises an ultrasound image processor 215 and a quantitative parameter processor 225.

In this embodiment, when the ultrasound apparatus 200 is used for hepatic steatosis detection, the ultrasound probe 201 includes various probes for B-mode ultrasound imaging, for example, a linear array probe, a convex array probe, a phased array probe, a volume probe, an instantaneous elasticity probe, etc. The user enables the ultrasound probe 201 to contact with a biological surface 208 stably, and sets ultrasound transmission parameters by means of the transmission and receiving controller 202, for example, setting a transmission frequency point, a focused intensity, a focused location, a scanning range, a scanning time, etc.

The transmission and receiving circuit 203 is used to switch between transmission and receiving. When it is necessary to transmit ultrasound waves, the transmission and receiving circuit 203 is switched to a state in which the transmission and receiving controller 202 is electrically connected to the ultrasound probe 201, such that the transmission and receiving controller 202 transfers the ultrasound transmission parameters to the ultrasound probe 201, and the ultrasound probe 201 generates corresponding ultrasound waves by electrical excitation. When it is necessary to receive the ultrasound echoes, the transmission and receiving circuit 203 is switched to a state in which the ultrasound probe 201 is electrically connected to the ultrasound echo signal processor 204, such that the ultrasound probe 201 converts the sensed ultrasound echo signals to electric signals and then transfers the electric signals to the ultrasound echo signal processor 204.

In this embodiment, the transmission and receiving circuit 203 divides the obtained ultrasound echoes into two paths, which respectively enter the first echo processor 214 and the second echo processor 224. The first echo processor 214 and the second echo processor 224 respectively perform filtering, amplification, beamforming and other processing on the obtained ultrasound echo signals. For ease of explanation, the ultrasound echo signal inputted to the first echo processor 214 is referred to as a first ultrasound echo signal, and the ultrasound echo signal inputted to the second echo processor 224 is referred to as a second ultrasound echo signal. In this embodiment, the first ultrasound echo signal and the second ultrasound echo signal may be the same ultrasound echo signals derived from the ultrasound waves transmitted at the same time, or may be different ultrasound echo signals derived from the ultrasound waves transmitted at different times.

Figure 3:
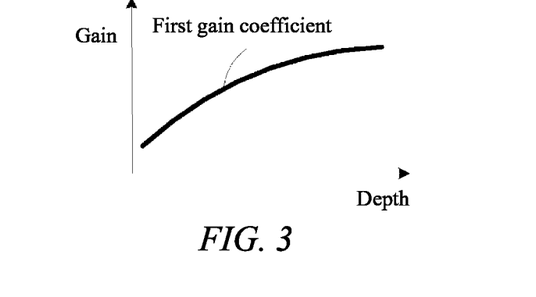
FIG. 3 is a schematic diagram of a first gain coefficient in an embodiment.
Figure 4:
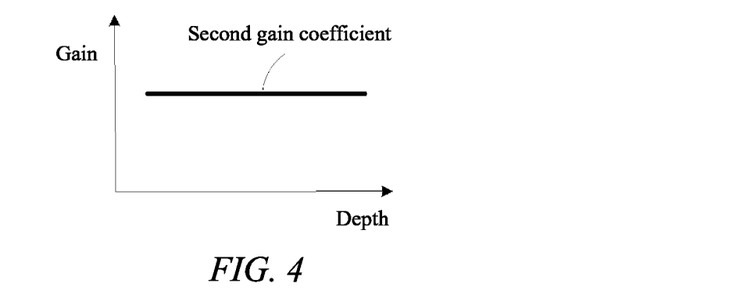
FIG. 4 is a schematic diagram of a second gain coefficient in an embodiment.

In order to improve the brightness consistency between the near field and far field of the B-mode ultrasound image, when the first ultrasound echo signal is amplified by the first echo processor 214, the gain coefficient thereof uses a first gain coefficient, which is a function related with a depth of a position where the ultrasound echo corresponding to the first ultrasound echo signal is generated in the target tissue, thereby setting different magnifications for the first ultrasound echo signal with different depths in the target tissue, for example, the greater the depth of the position where the ultrasound echo corresponding to the first ultrasound echo signal is generated in the target tissue is, the higher the magnification set for the first ultrasound echo signal is, as shown in FIG. 3. When the second ultrasound echo signal is amplified by the second echo processor 224, the gain compensation coefficient thereof uses a second gain coefficient, which is independent of the depth of the position where the ultrasound echo corresponding to the second ultrasound echo signal is generated in the target tissue, that is, the second gain does not change with the depth of the position where the ultrasound echo corresponding to the second ultrasound echo signal. For example, for the second ultrasound echo signal with different depths, the same magnification is set, such that the second ultrasound echo signal can still preserve the strong and weak contrast of the second ultrasound echo signal after being gain-compensated, so as to record the attenuation information caused by the ultrasound waves entering the tissue from shallow to deep, and preserve the original ultrasound echo information in the second ultrasound echo signal, as shown in FIG. 4.

In this embodiment, the ultrasound image processor 215 acquires ultrasound echo data after being processed by the first echo processor 214, and generates an ultrasound image, such as a B-mode image or a C-mode image, based on the acquired ultrasound echo data. The quantitative parameter processor 225 acquires ultrasound echo data after being processed by the second echo processor 224 to obtain the quantitative parameters of the biological tissue. The quantitative parameter includes at least one of quantitative parameter representing an ultrasound attenuation degree in the liver, quantitative parameter representing a difference between ultrasound echoes from the liver and another tissue, and quantitative parameter representing an ultrasound velocity in the liver.

Figure 5:
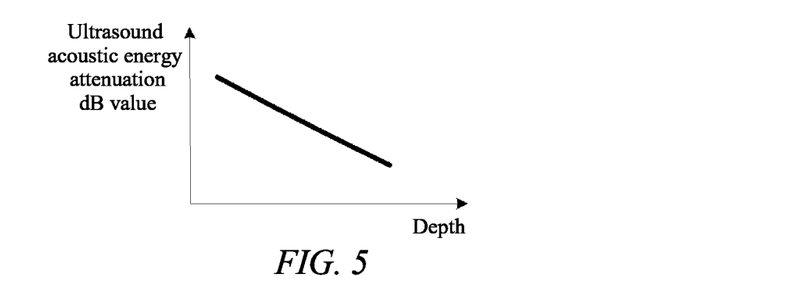
FIG. 5 is a schematic diagram of the relationship between the dB value of acoustic energy attenuation and depth in a biological tissue.

For the quantitative parameter representing the ultrasound attenuation degree in the liver, it is considered that when ultrasound waves propagate in a medium, the intensity of the ultrasound waves decreases with the propagation distance, and especially for a uniform tissue, the energy attenuation dB value of the ultrasound waves is approximately linearly proportional to the depth of the ultrasound waves in the target tissue and the current ultrasound frequency, as shown in FIG. 5. Therefore, according to the above linear relationship, by means of performing fitting or comparison on the ultrasound echo signal in the liver tissue, the average attenuation coefficient of the whole liver tissue can be obtained. The more serious the degree of hepatic steatosis in the liver tissue being, indicates that the higher the fat content in the liver tissue is, and the greater the attenuation coefficient of the liver tissue is accordingly. In an embodiment, the second ultrasound echo signal after being processed by the second echo processor 224 are fitted according to the depth of the position where the ultrasound echo corresponding to the second ultrasound echo signal is generated in the target tissue, which is performed by the quantitative parameter processor 225, so as to obtain a fitting straight line shown in FIG. 5. With the slope of the obtained fitting straight line (i.e., the attenuation coefficient) as a quantitative parameter representing the ultrasound attenuation degree in the liver, by which the fat content in the liver tissue can be evaluated.

In another embodiment, the quantitative parameter processor 225 selects the second ultrasound echo signal within two specific depth ranges from the second ultrasound echo signal being processed by the second echo processor 224, and the second ultrasound echo signal within two specific depth ranges is respectively near-field and far-field ultrasound echo signal. And a quantitative parameter representing ultrasound attenuation degree of the second ultrasound echo signal is obtained by means of performing comparison on the difference of the two signals for the near-field and far-field ultrasound echo signal, such as the two signals amplitude ratio, or the difference value in dB value of the two signals, or other parameters related to the two signals. Further, in an embodiment, the quantitative parameter processor 225 selects the second ultrasound echo signal at two depths from the second ultrasound echo signal being processed by the second echo processor 224, and then combines the selected second ultrasound echo signal and the difference in depth of the selected second echo signal in the target tissue, so as to calculate the quantitative parameters representing ultrasound attenuation degree in the liver. For example, "the difference value in dB value between a pair of ultrasound echo signal" and "the difference value in depth between a pair of ultrasound echo signal" are first obtained, then the ration between the two difference values can also be used as the quantitative parameter representing the ultrasound attenuation degree in the liver.

Figure 6:
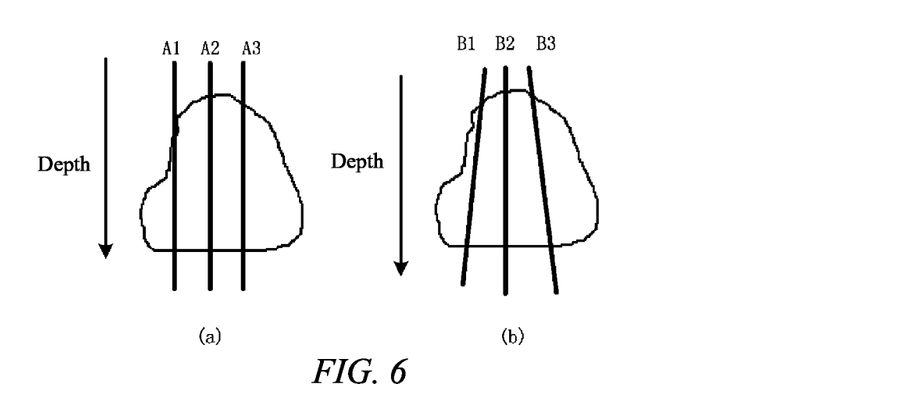
FIG. 6 is a schematic diagram of the propagation of ultrasound in different lateral positions in the biological tissue.

In some embodiments, according to the above linear relationship, other methods for obtaining the attenuation coefficient can also be used. For example, near-field and far-field echo data within a specific depth range are acquired, and the acquired two echo data are directly compared to obtain related parameters corresponding to the ultrasound attenuation, including the signal amplitude ratio or the difference value in dB value of the signal amplitude, etc.; or the acquired two echo data combine with the difference value in depth of the acquired two echo data in the target tissue, so as to calculate the attenuation coefficient of the liver. Furthermore, in order to measure the attenuation parameters of the biological tissue more accurately, some measurement and data processing methods can also be used. For example, since the attenuation of the ultrasound echo signals is related to both of the corresponding depth and the frequency of the ultrasound echo signals, multiple different frequencies can be used, and more accurate results can be obtained by means of combining the ultrasound echo data of corresponding frequencies. In addition to obtaining the attenuation parameter of the signal at different depths at a lateral position, the attenuation parameters of the signal at different lateral positions in the liver can also be separately calculated to obtain an overall tissue attenuation evaluation parameter. Alternatively, the overall signal attenuation parameter corresponding to the overall echo energy at multiple lateral positions at different depths is calculated to improve the accuracy of the quantitative parameters. As shown in FIG. 6, the lateral position described here represents a position in a different dimension from the direction of ultrasound waves propagation depth, and according to the different ultrasound transmission directions, the above lateral positions may be in parallel (such as the ultrasound echo signals at three different lateral positions A1, A2 and A3 in FIG. 6(*a*)), and may also be not in parallel (such as the ultrasound echo signals at three different lateral positions B1, B2 and B3 in FIG. 6(*b*)).

The quantitative parameter representing the echo difference between different tissues is obtained by means of comparing the second ultrasound echo signal of the liver and other different tissues. In the evaluation of hepatic steatosis, the doctor may need to compare the ultrasound echo signal difference of the liver and other different tissues. Taking the comparison between liver and kidney tissues as an example, the quantitative parameters representing the echo difference between the liver and the kidney can be obtained by only separately obtaining the ultrasound echo signals of the liver tissue and the kidney tissue and comparing the amplitudes of the ultrasound echo signals. The quantitative parameters can be selected as the amplitude ratio, the difference value in dB value of the amplitude, etc.

In the same way, the present disclosure can combine the overall comparison results of multiple echo data at different lateral positions to improve the accuracy of the obtained parameters.

The quantitative parameters representing the ultrasound velocity in the liver is obtained by means of comparing the signal-to-noise ratio or resolution of the second ultrasound echo signal at different ultrasound velocities. In different soft tissues, ultrasound waves have different propagation speeds. The average propagation speed of ultrasound waves in a soft tissue is about 1540 m/s, but the propagation speed of ultrasound waves in fat is about 1450 m/s. Therefore, providing the ultrasound velocity in the liver can also reflect the degree of hepatic steatosis to a certain extent.

In the process of receiving and processing ultrasound echo signals, the information received by the array elements are generally processed by beamforming so as to obtain an ultrasound echo with enhanced energy. However, the beamforming process is affected by the ultrasound velocity parameter. If the ultrasound velocity parameter is not appropriate, the overall signal-to-noise ratio of the ultrasound echo signal obtained after beamforming will be poor, resulting in an unclear image and low resolution. Therefore, by means of comparing the performance, such as signal-to-noise ratio or resolution of the echo obtained after beamforming at different ultrasound velocities, the ultrasound velocity corresponding to the highest performance can be used as the current measured ultrasound velocity.

In this embodiment, the quantitative parameters further include a quantitative parameter representing the size of the liver, which is obtained on the basis of the obtained ultrasound echo signal or the ultrasound image. For example, the size of the normal liver is 25 cm in long diameter, 15 cm in vertical diameter, and 16 cm in anteroposterior diameter. The system can calculate parameters related to the size of the liver, such as the area, volume, long diameter, vertical diameter and anteroposterior diameter, by means of automatically detecting the liver edge or manually confirming the liver edge by the doctor on the basis of the B-mode image of the liver tissue. In addition, the ultrasound apparatus 200 may also calculate the quantitative parameters representing the size of the liver by means of data processing on the basis of an ultrasound echo signal (e.g., the first ultrasound echo signal or the second ultrasound echo signal).

Figure 7:
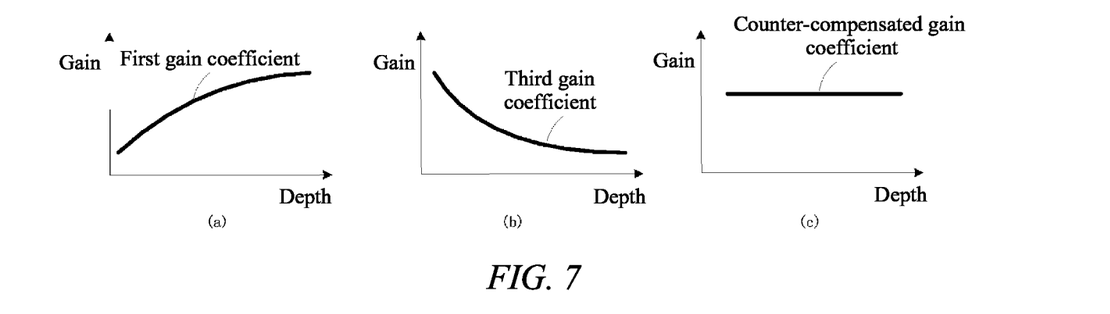
FIG. 7 is a schematic diagram of the interaction of the two gain coefficients in an embodiment.
Figure 8:
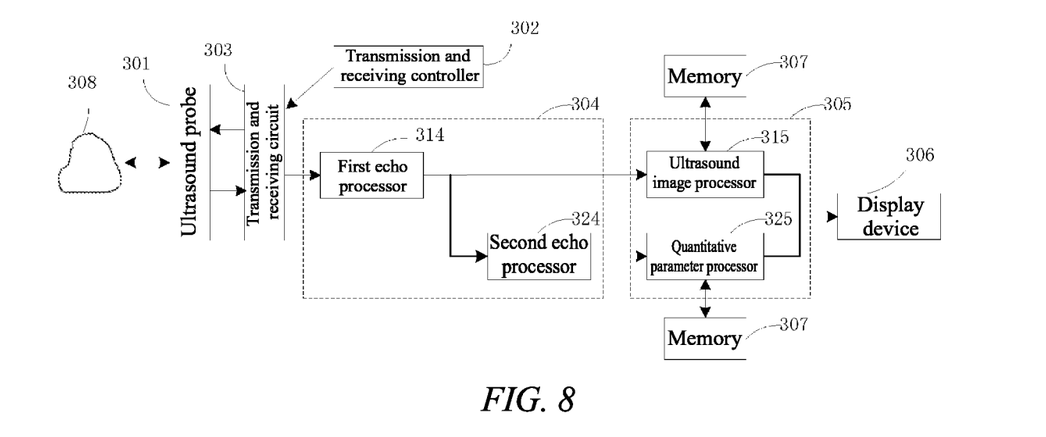
FIG. 8 is a structural schematic diagram of an ultrasound hepatic steatosis detection apparatus in another embodiment.

Referring to FIGS. 7 and 8, another embodiment is provided. The difference between this embodiment and the embodiment I is the method of gain compensation in the ultrasound echo signal processor.

In this embodiment, gain compensation is performed firstly on the received echo data (including the first ultrasound echo signal and the second ultrasound echo signal) with a first gain coefficient, then the gain-compensated echo data is divided into two paths of the first ultrasound echo signal and the second ultrasound echo signal, and gain counter-compensation is then performed on the second ultrasound echo signal with a third gain coefficient, so as to restore the signal attenuation of ultrasound waves transferred from shallow to deep in the target tissue.

Referring to FIG. 8, in this embodiment, the ultrasound apparatus 300 comprises an ultrasound probe 301, a transmission and receiving controller 302, a transmission and receiving circuit 303, an ultrasound echo signal processor 304, a data processor 305, a display device 306 and a memory 307. The ultrasound probe 301, the transmission and receiving controller 302, the transmission and receiving circuit 303, the data processor 305, the display device 306 and the memory 307 are the same as those in the embodiment I, which will not be repeated here. The ultrasound echo signal processor 304 comprises a first echo processor 314 and a second echo processor 324. The first echo processor 314 firstly receives the ultrasound echo signal received by the transmission and receiving circuit 303, and performs filtering, amplification, beamforming and other processing for the received ultrasound echo signal. When being processed by amplification, the ultrasound echo signal can be processed according to the requirements of a desired ultrasound image. For example, for the purpose of enhancing image quality, gain compensation is performed on the ultrasound echo signal with the first gain coefficient. The first gain coefficient is related to the depth of the position where the ultrasound echo corresponding to the obtained ultrasound echo signal is generated in the target tissue. For different depths, the gain coefficients are different. For example, the deeper the depth, the greater the first gain coefficient, as shown in FIG. 7a. Then the first echo processor 314 divides the processed ultrasound echo signal into two paths, which respectively enter the ultrasound image processor 315 and the second echo processor 324. For ease of explanation, the ultrasound echo signal inputted to the first echo processor 314 is referred to as the first ultrasound echo signal, and the ultrasound echo signal inputted to the second echo processor 324 is referred to as the second ultrasound echo signal. In the second echo processor 324, the second ultrasound echo signal is amplified by being performed by a third gain coefficient. The third gain coefficient is also a depth-related function, such that different magnifications can be set for the second ultrasound echo signals at different depths. For example, the greater the depth, the lower the magnification, as shown in FIG. 7(b). The gain coefficient of the second ultrasound echo signal after gain counter-compensation by the second echo processor 324 is substantially a fixed value, as shown in FIG. 7(c), such that the second ultrasound echo signal can still preserve the strong and weak contrast of the gain-compensated ultrasound echo signal, so as to record the attenuation caused by the ultrasound waves entering the tissue from shallow to deep and preserve the original ultrasound echo information in the second ultrasound echo signal. Therefore, the second ultrasound echo signal after being processed by the second echo processor 324 preserves the original ultrasound echo information as much as possible, and is input to the quantitative parameter processor 325 for calculation and processing of quantitative parameters.

In an embodiment, a transmission/receiving control method by which the conventional B-mode imaging is obtained is used. As B-mode imaging is the basic function of ultrasound imaging apparatus, in the present disclosure, since no additional transmission/receiving sequence is introduced, the present disclosure can be applied to most of the ultrasound systems which is of different costs, such as monochrome ultrasonography, low-end color Doppler ultrasonography, high-end multi-function color Doppler ultrasonography, etc. The ultrasound echo received at a certain moment is an original ultrasound echo signal which can be used to generate a B-mode image. Under this option, the same sequence can be used to generate a B-mode image and also to calculate quantitative parameters.

Furthermore, the transmission/receiving control sequence may also be selected to generate, in addition to a conventional B-mode imaging control sequence, an independent control sequence dedicated to calculation of quantitative parameters, in which the control parameters, such as transmission frequency point, focused intensity, focused location, scanning range and scanning time, can also be different from the conventional B-mode imaging. Under this option, the B-mode sequence is used to generate a B-mode image, and the independent control sequence is used to calculate the quantitative parameters.

Figure 9:
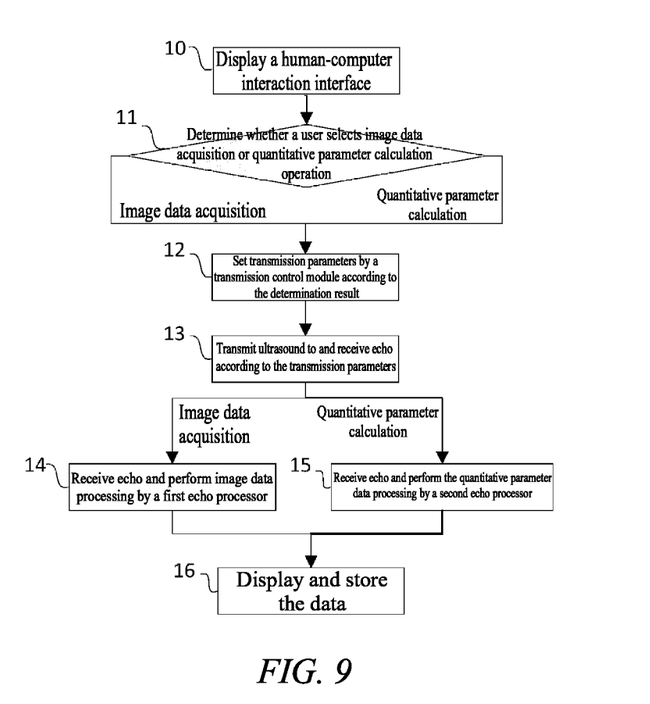
FIG. 9 is a schematic diagram of a procedure of ultrasound detection of hepatic steatosis in another embodiment.

Referring to FIG. 9, through a human-computer interaction interface, the user can select different transmission/receiving sequences, so as to control the system to perform image data acquisition or quantitative parameter calculation operation. The specific steps are as follows:

step 10, displaying a human-computer interaction interface to provide a user with operation options, wherein the operation options including ultrasound image data acquisition and quantitative parameter calculation operation.

step 11, determining a user's operation selection result;

step 12, setting ultrasound transmission parameters according to the above determination result, for example, wherein the ultrasound transmission parameters including the transmission frequency point, focused intensity, focused location, scanning range, scanning time, etc.;

step 13, transmitting ultrasound waves to and receiving echo from a region of interest of the biological tissue according to the set transmission parameters;

step 14, when the user selecting the image data acquisition operation, the first echo processor receiving echo data and performing gain compensation on the received echo data to enhance the image data quality and further process the enhanced image data;

step 15, when the user selecting the quantitative parameter calculation operation, the second echo processor receiving the echo data and performing the corresponding gain compensation on the received echo data to preserve the original ultrasound echo information and further process the quantitative parameter data; and step 16, storing the results which are obtained respectively by echo processing and data processing in a memory, or displaying the stored results on the human-computer interaction interface for the user.

The process of obtaining tissue ultrasound images and quantitative parameter calculation results by means of the above method can be implemented by the system automatically running responding to a user selection operation, or can be implemented step by step through manual triggering by a user, which will not be listed here.

In an embodiment, an ultrasound imaging method using the above system may comprises:

transmitting an ultrasound wave to a target tissue and receiving an ultrasound echo from the target tissue to obtain an ultrasound echo signal, the target tissue being a tissue of a liver;

performing a gain compensation for enhancing image quality on a first ultrasound echo signal to be used for obtaining an ultrasound image of the target tissue;

performing a gain compensation for preserving original information on a second ultrasound echo signal to be used for calculating a quantitative parameter of the liver;

generating the ultrasound image of the target tissue according to the processed first ultrasound echo signal;

calculating the quantitative parameter of the liver according to the processed second ultrasound echo signal; and displaying the ultrasound image and the quantitative parameter.

In an embodiment, performing gain compensation on the first ultrasound echo signal to be used for obtaining an ultrasound image of the target tissue, for the purpose of enhancing image quality may comprise: performing gain compensation on the first ultrasound echo signal with a first gain coefficient which changes with a depth of a position where the ultrasound echo corresponding to the first ultrasound echo signal is generated in the target tissue.

In an embodiment, performing gain compensation, for the purpose of preserving original information, on the second ultrasound echo signal to be used for calculating the quantitative parameter of the liver comprises: performing gain compensation on the second ultrasound echo signal with a second gain coefficient which is fixed.

In an embodiment, performing gain compensation, for the purpose of preserving original ultrasound echo information, on the second ultrasound echo signal to be used for calculating the quantitative parameter of the liver comprises: firstly performing gain compensation on the second ultrasound echo signal with a first gain coefficient, and then performing gain compensation on the gain-compensated second ultrasound echo signal with a third gain coefficient, such that the resultant gain coefficient on the second ultrasound echo signal does not change with a depth of a position where the ultrasound echo corresponding to the second ultrasound echo signal is generated in the target tissue.

In an embodiment, performing gain compensation, for the purpose of preserving original information, on the second ultrasound echo signal to be used for calculating the quantitative parameter of the liver comprises: performing gain compensation, for the purpose of preserving original ultrasound information, on the second ultrasound echo signal to be used for calculating the quantitative parameter of the liver.

In an embodiment, the quantitative parameter may include a quantitative parameter representing the ultrasound attenuation degree in the liver, a quantitative parameter representing a difference between ultrasound echoes from the liver and another tissue, and a quantitative parameter representing an ultrasound velocity in the liver; wherein, the quantitative parameter representing the ultrasound attenuation degree in the liver is obtained by fitting or comparing the gain-compensated second ultrasound echo signal based on a depth, the quantitative parameter representing the difference between ultrasound echoes from the liver and the another tissue is obtained by comparing the gain-compensated second ultrasound echo signals from the liver and the another tissue, and the quantitative parameter representing the ultrasound velocity in the liver is obtained by comparing signal-to-noise ratios or ultrasound image resolutions of the gain-compensated second ultrasound echo signals obtained in different ultrasound velocities.

In an embodiment, the quantitative parameter may further comprises a quantitative parameter representing the size of the liver, and the quantitative parameter representing the size of the liver is obtained on the basis of the obtained ultrasound echo signal or the ultrasound image.

A person skilled in the art may understand that all or some of the functions of the various methods in the above implementations may be implemented by means of hardware or by means of a computer program. When all or some of the functions in the above implementations are implemented by means of a computer program, the program may be stored in a computer-readable storage medium, and the storage medium may comprise: a read-only memory, a random access memory, a magnetic disk, an optical disk, a hard disk, and the like, and the program is executed by a computer to implement the above functions. For example, the program is stored in a memory of an apparatus, and when the program in the memory is executed by means of a processor, all or some of the above functions can be implemented. In addition, when all or some of the functions in the above implementations are implemented by means of a computer program, the program may also be stored in a storage medium such as a server, another computer, a magnetic disk, an optical disk, a flash disk, or a mobile hard disk, may be saved in a memory of a local apparatus through downloading or copying, or version updating may be performed on a system of the local apparatus. When the program in the memory is executed by means of a processor, all or some of the functions in the above implementations can be implemented.

The description has been made with reference to various exemplary embodiments herein. However, those skilled in the art would have appreciated that changes and modifications could have been made to the exemplary embodiments without departing from the scope herein. For example, various operation steps and components for performing operation steps may be implemented in different ways according to a specific application or considering any number of cost functions associated with the operation of the system (for example, one or more steps may be deleted, modified or incorporated into other steps).

In addition, as understood by those skilled in the art, the principles herein may be reflected in a computer program product on a computer-readable storage medium that is pre-installed with computer-readable program codes. Any tangible, non-transitory computer-readable storage medium can be used, including magnetic storage apparatuses (hard disks, floppy disks, etc.), optical storage apparatuses (CD-ROM, DVD, Blu Ray disks, etc.), flash memory, and/or the like. These computer program instructions can be loaded onto a general-purpose computer, a dedicated computer, or other programmable data processing apparatus to form a machine, such that these instructions executed on a computer or other programmable data processing device can generate a device that implements a specified function. These computer program instructions can also be stored in a computer-readable memory that can instruct a computer or other programmable data processing device to operate in a specific manner, such that the instructions stored in the computer-readable memory can form a manufactured product, including an implementation apparatus that implements a specified function. The computer program instructions can also be loaded onto a computer or other programmable data processing apparatus, such that a series of operating steps are performed on the computer or other programmable apparatus to produce a computer-implemented process, such that the instructions executed on a computer or other programmable data processing apparatus can provide steps for implementing specified functions.

Although the principles herein have been shown in various embodiments, many modifications of structures, arrangements, ratios, elements, materials, and components that are particularly suitable for specific environments and operating requirements can be made without departing from the principles and scope of the present disclosure. The above modifications and other changes or amendments will be included within the scope herein.

The foregoing specific description has been described with reference to various embodiments. However, those skilled in the art would have appreciated that various modifications and changes could have been made without departing from the scope of the present disclosure. Therefore, consideration of the present disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprising" and any other variants thereof used herein are non-exclusive, such that the process, method, document, or apparatus that includes a list of elements includes not only these elements, but also other elements that are not explicitly listed or do not belong to the process, method, system, document, or apparatus. Furthermore, the term "coupling" and any other variations thereof used herein refer to physical connection, electrical connection, magnetic connection, optical connection, communication connection, functional connection, and/or any other connection.

Those skilled in the art will recognize that many changes can be made to the details of the above-described embodiments without departing from the basic principles of the present invention. Therefore, the scope of the present invention should be determined only by the claims as follows.

The invention claimed is:

1. An ultrasound apparatus, comprising:
   an ultrasound probe configured to transmit ultrasound waves to a liver and receive ultrasound echoes from the liver;
   a transmission and receiving controller configured to control the ultrasound probe to transmit the ultrasound waves to the liver and receive the ultrasound echoes to obtain ultrasound echo signals, wherein the ultrasound echo signals comprises a first ultrasound echo signal and a second ultrasound echo signal;
   an ultrasound echo signal processor configured to perform a first gain compensation for enhancing image quality on the first ultrasound echo signal for obtaining an ultrasound image of the liver, and a second gain compensation for preserving ultrasound attenuation information of the second ultrasound echo signal on the second ultrasound echo signal for calculating a quantitative parameter of the liver;
   a data processor configured to generate the ultrasound image of the liver according to the processed first ultrasound echo signal, calculate the quantitative parameter of the liver according to the processed second ultrasound echo signal, and output the ultrasound image and the quantitative parameter; and
   a display device configured to display the ultrasound image and the quantitative parameter.

2. The ultrasound apparatus of claim 1, wherein the ultrasound echo signal processor comprises a first ultrasound echo signal processor and a second ultrasound echo signal processor, the first echo signal processor being configured to perform the first gain compensation for enhancing image quality on the first ultrasound echo signal with a first gain coefficient which changes with a depth of a position where an ultrasound echo corresponding to the first ultrasound echo signal is generated in the liver, and the second ultrasound echo signal processor being configured to perform the second gain compensation for preserving ultrasound attenuation information of the second ultrasound echo signal with a fixed second gain coefficient.

3. The ultrasound apparatus of claim 1, wherein the ultrasound echo signal processor is configured to perform a gain compensation on the second ultrasound echo signal with a first gain coefficient, and to perform a gain compensation on the gain-compensated second ultrasound echo signal with a third gain coefficient, such that a resultant gain coefficient on the second ultrasound echo signal does not change with a depth of a position where an ultrasound echo corresponding to the second ultrasound echo signal is generated in the liver.

4. The ultrasound apparatus of claim 1, wherein the ultrasound echo signal processor is configured to perform the second gain compensation for preserving the ultrasound attenuation information of the second ultrasound echo signal on the second ultrasound echo signal by preserving strong and weak contrast of the second ultrasound echo signal.

5. The ultrasound apparatus of claim 1, wherein the transmission and receiving controller is configured to control the ultrasound probe to transmit a first ultrasound wave to the liver to obtain the first ultrasound echo signal with a first transmission/receiving sequence, and to control the ultrasound probe to transmit a second ultrasound wave to the liver to obtain the second ultrasound echo signal with a second transmission/receiving sequence.

6. The ultrasound apparatus of claim 1,
wherein the quantitative parameter comprises at least one of a quantitative parameter representing an ultrasound attenuation degree in the liver, a quantitative parameter representing a difference between ultrasound echoes from the liver and another tissue, or a quantitative parameter representing an ultrasound velocity in the liver;
wherein the quantitative parameter representing the ultrasound attenuation degree in the liver is obtained by fitting or comparing the gain-compensated second ultrasound echo signal based on a depth, the quantitative parameter representing the difference between ultrasound echoes from the liver and the another tissue is obtained by comparing the gain-compensated second ultrasound echo signals from the liver and the another tissue, and the quantitative parameter representing the ultrasound velocity in the liver is obtained by comparing signal-to-noise ratios or resolutions of gain-compensated second ultrasound echo signals obtained at different ultrasound velocities.

7. The ultrasound apparatus of claim 1, wherein the quantitative parameter further comprises a quantitative parameter representing a size of the liver, wherein the quantitative parameter representing the size of the liver is obtained according to the obtained ultrasound echo signal or the ultrasound image.

8. The ultrasound apparatus of claim 1, wherein the display device is configured to simultaneously or alternately display the ultrasound image and the quantitative parameter according to a selection of a user.

9. An ultrasound-based liver examination device, comprising:
a receiving circuit configured to acquire ultrasound echo signals obtained by scanning a liver with ultrasound waves, wherein the ultrasound echo signals comprises a first ultrasound echo signal and a second ultrasound echo signal;
an ultrasound echo signal processor configured to perform a first gain compensation for enhancing image quality on the first ultrasound echo signal for obtaining an ultrasound image of the liver and a second gain compensation for preserving ultrasound attenuation information of the second ultrasound echo signal on the second ultrasound echo signal for calculating a quantitative parameter of the liver; and
a data processor configured to generate the ultrasound image of the liver according to the processed first ultrasound echo signal and calculate the quantitative parameter of the liver according to the processed second ultrasound echo signal.

10. The device of claim 9, wherein the ultrasound echo signal processor is configured to perform a gain compensation on the first ultrasound echo signal with a first gain coefficient which changes with a depth of a position where an ultrasound echo corresponding to the first ultrasound echo signal is generated in the liver to implement the first gain compensation for enhancing image quality on the first ultrasound echo signal.

11. The device of claim 9, wherein the ultrasound echo signal processor is configured to perform a gain compensation on the second ultrasound echo signal with a fixed second gain coefficient to implement the second gain compensation for preserving the ultrasound attenuation information of the second ultrasound echo signal.

12. The device of claim 9, wherein the ultrasound echo signal processor is configured to perform a gain compensation on the second ultrasound echo signal with a first gain coefficient, and to perform a gain compensation on the gain-compensated second ultrasound echo signal with a third gain coefficient, such that a resultant gain coefficient on the second ultrasound echo signal does not change with a depth of a position where an ultrasound echo corresponding to the second ultrasound echo signal is generated in the liver to implement the second gain compensation for preserving the ultrasound attenuation information of the second ultrasound echo signal.

13. The device of claim 9, wherein the ultrasound echo signal processor is configured to perform the second gain compensation for preserving the ultrasound attenuation information of the second ultrasound echo signal on the second ultrasound echo signal by preserving strong and weak contrast of the second ultrasound echo signal.

14. The device of claim 9, wherein the first ultrasound echo signal is obtained by controlling a probe to transmit a first ultrasound wave to the liver with a first transmission/receiving sequence, and the second ultrasound echo signal is obtained by controlling the probe to transmit a second ultrasound wave to the liver with a second transmission/receiving sequence.

15. The device of claim 9,
wherein the quantitative parameter comprises at least one of a quantitative parameter representing an ultrasound attenuation degree in the liver, a quantitative parameter representing a difference between ultrasound echoes from the liver and another tissue, or a quantitative parameter representing an ultrasound velocity in the liver; and
wherein the quantitative parameter representing the ultrasound attenuation degree in the liver is obtained by fitting or comparing the gain-compensated second ultrasound echo signal based on a depth, the quantitative parameter representing the difference between ultrasound echoes from the liver and the another tissue is obtained by comparing the gain-compensated second ultrasound echo signals from the liver and said another tissue, and the quantitative parameter representing the ultrasound velocity in the liver is obtained by comparing signal-to-noise ratios or ultrasound image resolutions of the gain-compensated second ultrasound echo signals obtained at different ultrasound velocities.

16. The device of claim 15, wherein the quantitative parameter comprises a quantitative parameter representing a size of the liver, wherein the quantitative parameter representing the size of the liver is obtained according to the ultrasound echo signals or the ultrasound image.

17. An ultrasound imaging method, comprising:
transmitting ultrasound waves to a liver and receiving ultrasound echoes from the liver to obtain ultrasound echo signals, wherein the ultrasound echo signals comprises a first ultrasound echo signal and a second ultrasound echo signal;
performing a first gain compensation for enhancing image quality on the first ultrasound echo signal for obtaining an ultrasound image of the liver;
performing a second gain compensation for preserving ultrasound attenuation information of the second ultrasound echo signal on a second ultrasound echo signal for calculating a quantitative parameter of the liver;
generating the ultrasound image of the liver according to the processed first ultrasound echo signal;
calculating the quantitative parameter of the liver according to the processed second ultrasound echo signal; and
displaying the ultrasound image and the quantitative parameter.

18. The method of claim 17, wherein performing the first gain compensation for enhancing image quality on the first ultrasound echo signal for obtaining the ultrasound image of the liver comprises: performing a gain compensation on the first ultrasound echo signal with a first gain coefficient which changes with a depth of a position where an ultrasound echo corresponding to the first ultrasound echo signal is generated in the liver.

19. The method of claim 17, wherein performing the second gain compensation for preserving the ultrasound attenuation information of the second ultrasound echo signal on the second ultrasound echo signal for calculating the quantitative parameter of the liver comprises: performing a gain compensation on the second ultrasound echo signal with a fixed second gain coefficient.

20. The method of claim 17, wherein performing the second gain compensation for preserving the ultrasound attenuation information of the second ultrasound echo signal on the second ultrasound echo signal for calculating the quantitative parameter of the liver comprises: performing a gain compensation on the second ultrasound echo signal with a first gain coefficient and performing a gain compensation on the gain-compensated second ultrasound echo signal with a third gain coefficient such that a resultant gain coefficient on the second ultrasound echo signal does not change with a depth of a position where an ultrasound echo corresponding to the second ultrasound echo signal is generated in the liver.

* * * * *